(12) United States Patent
Stephens et al.

(10) Patent No.: US 10,765,828 B2
(45) Date of Patent: Sep. 8, 2020

(54) ADJUSTABLE TENSION DEVICE FOR CPAP MASK

(71) Applicant: KONINKLIJKE PHILIPS N.V., Eindhoven (NL)

(72) Inventors: Nathaniel Stephens, Pittsburgh, PA (US); Marcel Douglas Jaffre, Wendel, PA (US); Duon Alex Truong, Plum Borough, PA (US)

(73) Assignee: Koninklijke Philips N.V., Eindhoven (NL)

(*) Notice: Subject to any disclaimer, the term of this patent is extended or adjusted under 35 U.S.C. 154(b) by 396 days.

(21) Appl. No.: 15/533,507

(22) PCT Filed: Dec. 7, 2015

(86) PCT No.: PCT/IB2015/059422
§ 371 (c)(1),
(2) Date: Jun. 6, 2017

(87) PCT Pub. No.: WO2016/092462
PCT Pub. Date: Jun. 16, 2016

(65) Prior Publication Data
US 2017/0368288 A1 Dec. 28, 2017

Related U.S. Application Data

(60) Provisional application No. 62/089,357, filed on Dec. 9, 2014.

(51) Int. Cl.
*A61M 16/06* (2006.01)

(52) U.S. Cl.
CPC ........ *A61M 16/0622* (2014.02); *A61M 16/06* (2013.01); *A61M 16/0683* (2013.01); *A61M 2016/0661* (2013.01)

(58) Field of Classification Search
CPC ...... A61M 2016/0661; A61M 16/0683; A61M 16/0622; A61M 16/06
See application file for complete search history.

(56) References Cited

U.S. PATENT DOCUMENTS

| | | | |
|---|---|---|---|
| 7,954,204 B2 | 6/2011 | Hammerslag |
| 8,091,182 B2 | 1/2012 | Hammerslag |
| 8,424,168 B2 | 4/2013 | Soderberg |
| 8,490,623 B2 | 7/2013 | Berthon-Jones et al. |

(Continued)

FOREIGN PATENT DOCUMENTS

| | | |
|---|---|---|
| CN | 101496646 A | 8/2009 |
| EP | 2583713 A2 | 4/2013 |

(Continued)

*Primary Examiner* — Timothy A Stanis
*Assistant Examiner* — Cana A Gallegos
(74) *Attorney, Agent, or Firm* — Michael W. Haas

(57) ABSTRACT

A cushion tension assembly for a respiratory interface device is provided. Cushion tension assembly includes an adjustment assembly and a number of tension members. Each tension member is operatively coupled to the adjustment assembly and is operatively coupled to the cushion body. In this configuration, the adjustment assembly is structured to move cushion body between a first configuration in which the cushion body provides a generally continuous seal, and a second configuration in which the cushion body provides a more complete seal.

6 Claims, 18 Drawing Sheets

(56) References Cited

U.S. PATENT DOCUMENTS

| | | | |
|---|---|---|---|
| 8,516,662 B2 | 8/2013 | Goodman | |
| 8,596,275 B2 | 12/2013 | Matula et al. | |
| 10,201,678 B2 | 2/2019 | Guney et al. | |
| 2007/0044804 A1* | 3/2007 | Matula, Jr. ............ | A61M 16/06 128/206.21 |
| 2008/0072909 A1 | 3/2008 | Sherman | |
| 2014/0338671 A1 | 11/2014 | Chodkowski | |
| 2015/0007824 A1* | 1/2015 | Chodkowski ......... | A61M 16/06 128/206.24 |

FOREIGN PATENT DOCUMENTS

| | | | |
|---|---|---|---|
| FR | 2397199 A1 | 2/1979 | |
| WO | WO2013084110 A1 | 6/2013 | |
| WO | WO2013128309 A1 | 9/2013 | |
| WO | WO-2013128324 A2 * | 9/2013 | ............ A61M 16/06 |

* cited by examiner

ADJUSTABLE TENSION DEVICE FOR CPAP MASK

CROSS-REFERENCE TO RELATED APPLICATIONS

This patent application claims the priority benefit under 35 U.S.C. § 371 of international patent application no. PCT/IB2015/059422, filed Dec. 7, 2015, which claims the priority benefit under 35 U.S.C. § 119(e) of U.S. Provisional Application No. 62/089,357 filed on Dec. 9, 2014, the contents of which are herein incorporated by reference.

BACKGROUND OF THE INVENTION

1. Field of the Invention

The present invention pertains to patient interface devices for delivering a flow of breathing gas to a patient during, for example, respiratory therapy, and, in particular, to a patient interface device including a cushion tension assembly.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, or obstructive sleep apnea (OSA).

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient so that a flow of breathing gas can be delivered from a pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the mask components of the device in a tight enough seal against the patient's face without discomfort.

A typical cushion includes a thin sealing membrane backed by a thicker support structure, both mounted to a rigid faceplate. As used herein, the type of seal provided by such a cushion is a "generally continuous seal." Such a cushion, however, may not conform as well as possible to a user's facial contour. A "more complete seal" may be established with minor changes to the shape of the cushion. That is, a generic cushion can be adapted to provide a more complete seal on a specific user by reconfiguring the cushion, including reconfiguring the cushion while in use.

SUMMARY OF THE INVENTION

One embodiment of the presently disclosed concept provides a cushion tension assembly for a respiratory interface device. Cushion tension assembly includes an adjustment assembly and a number of tension members. Each tension member is operatively coupled to the adjustment assembly and to the cushion body. In this configuration the adjustment assembly is structured to move cushion body between a first configuration in which the cushion body provides a generally continuous seal, and a second configuration in which the cushion body provides a more complete seal.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

It is a further object of this invention to provide a method of using a respiratory interface device including an adjustment assembly, the method including positioning the respiratory interface device over the user's face, seating the cushion body engagement portion against the user's face so that cushion body engagement portion provides a generally continuous seal, and actuating the cushion tension assembly so that the cushion body moves between a first configuration and a second configuration.

DETAILED DESCRIPTION OF EXEMPLARY EMBODIMENTS

Figure 1:
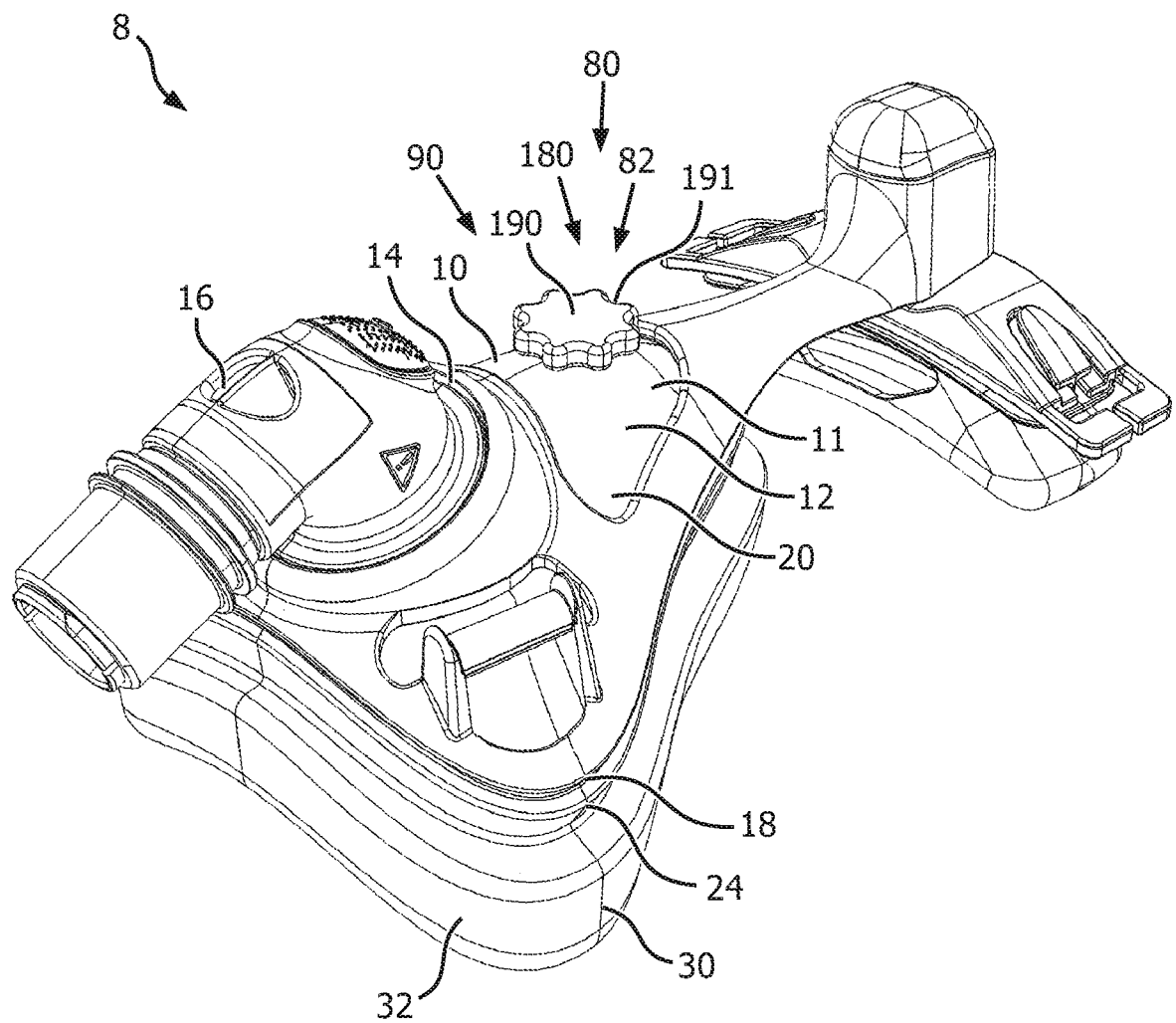
FIG. 1 is an isometric view of one embodiment of a respiratory interface assembly.
Figure 2:
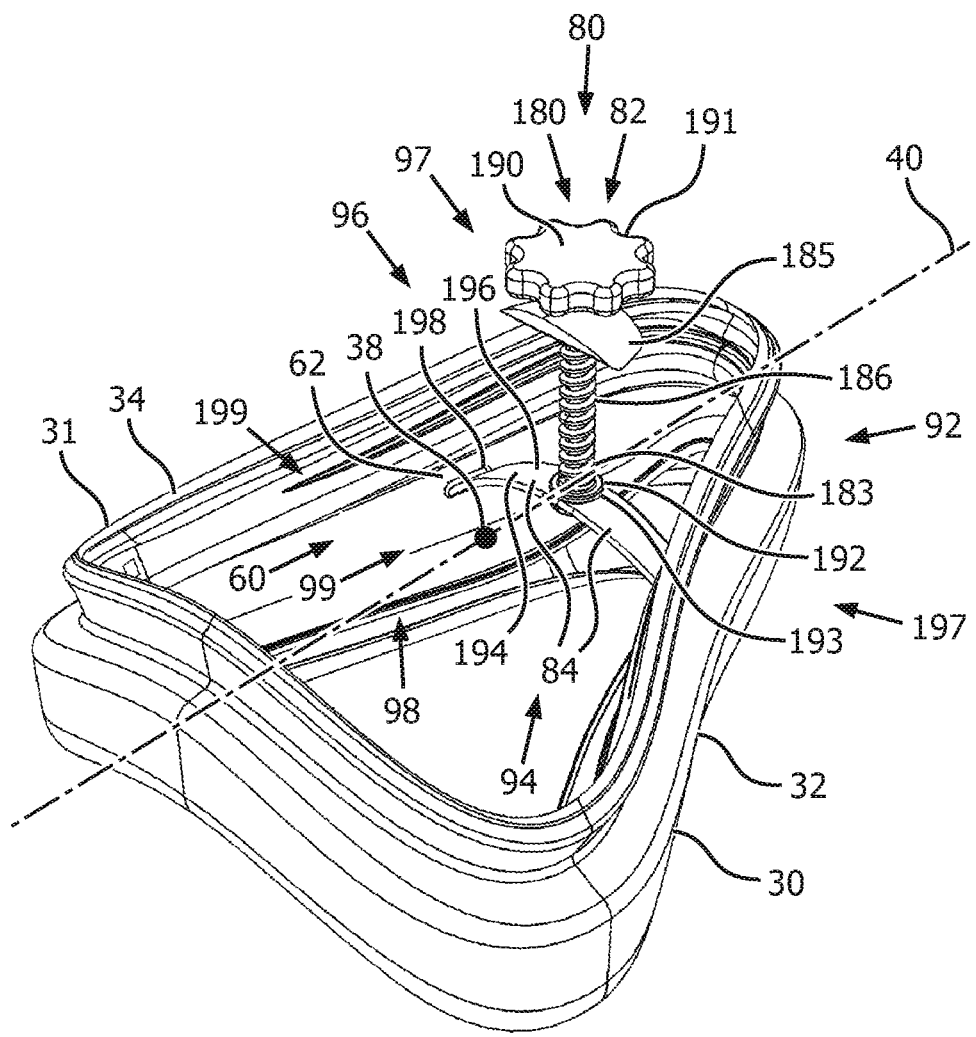
FIG. 2 is a partial isometric view of the respiratory interface assembly of FIG. 1.
Figure 3:
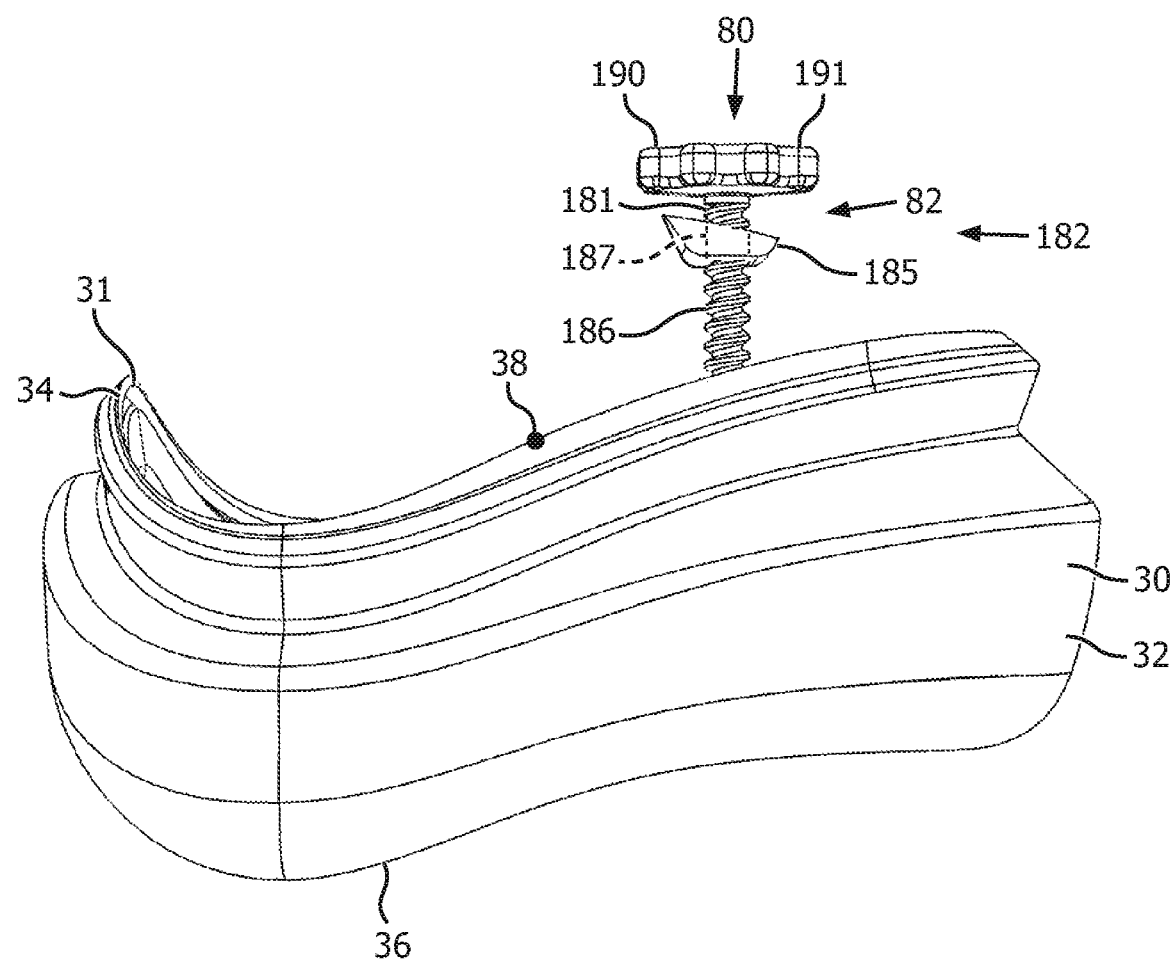
FIG. 3 is a partial side view of the respiratory interface assembly of FIG. 1.
Figure 4:
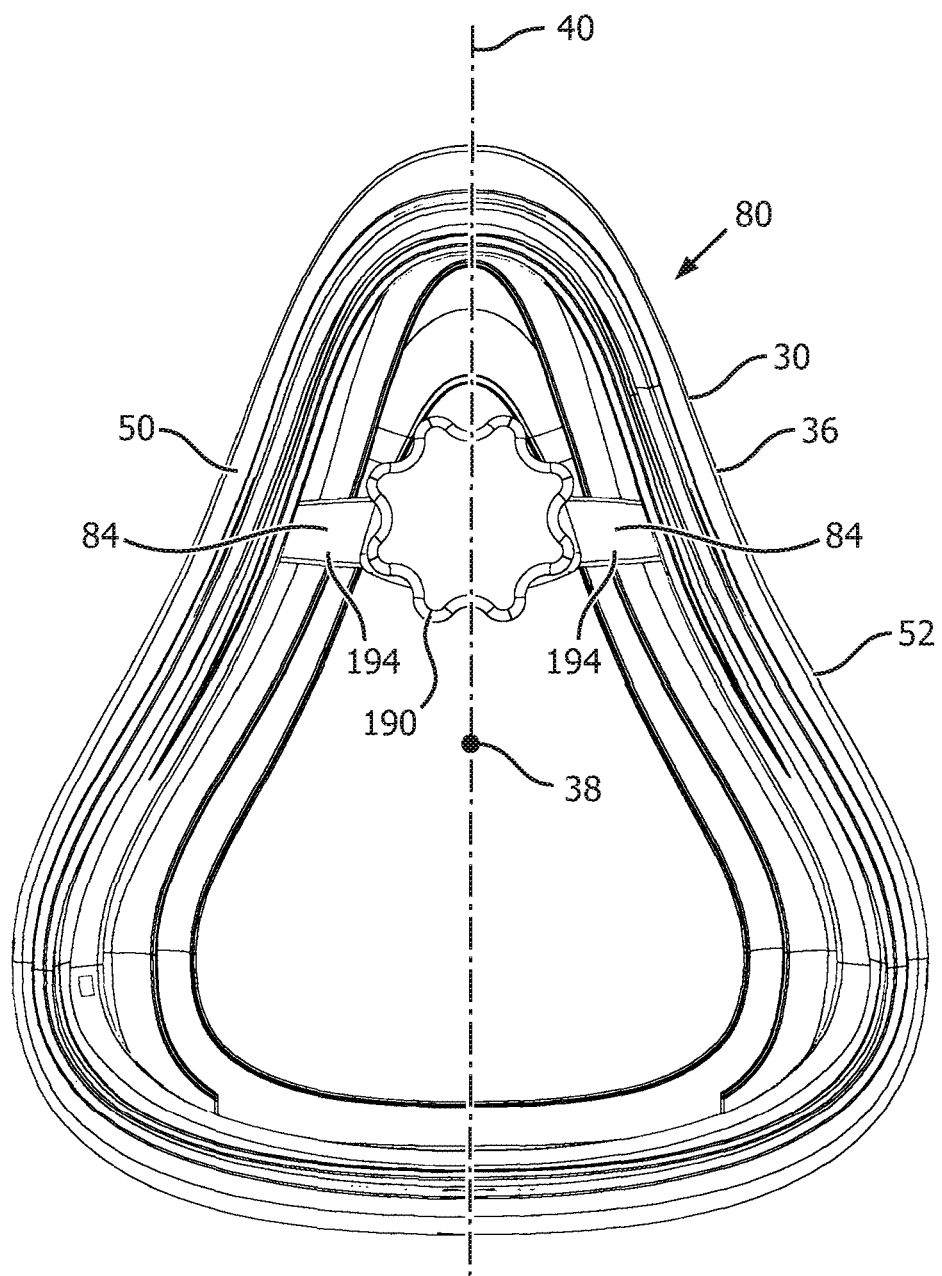
FIG. 4 is a partial front view of the respiratory interface assembly of FIG. 1.
Figure 4A:
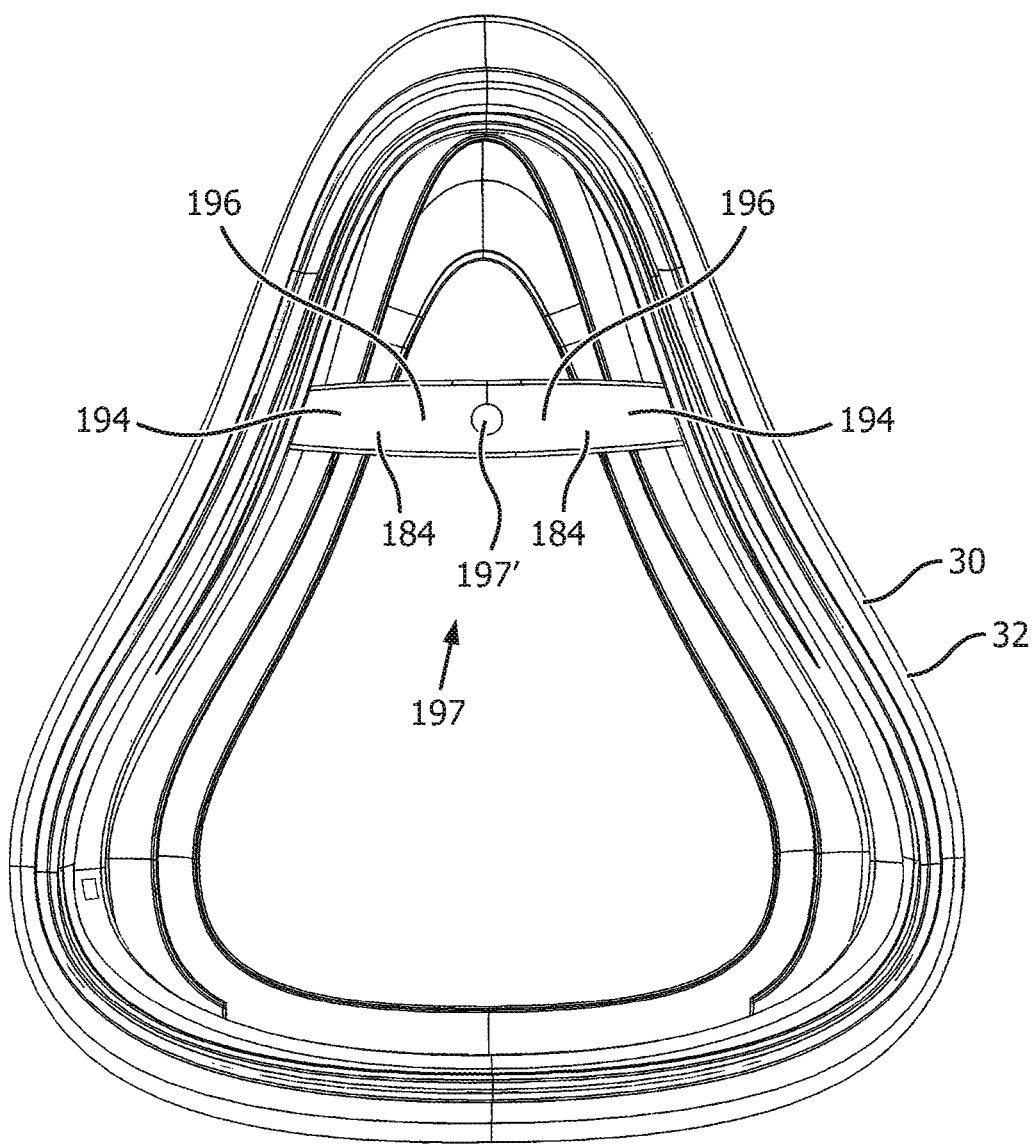
FIG. 4A is another partial front view of the respiratory interface assembly of FIG. 1.
Figure 5:
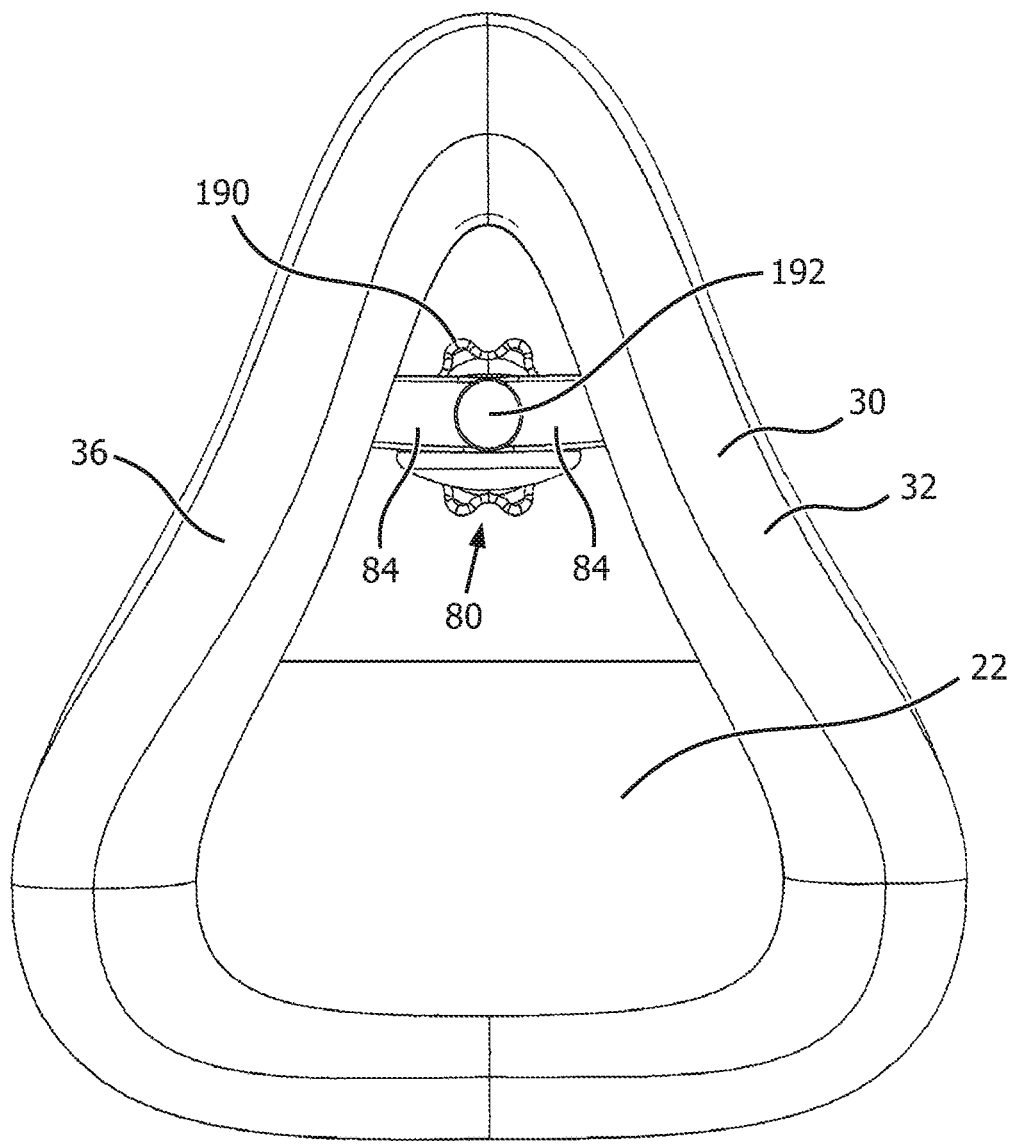
FIG. 5 is a partial back view of the respiratory interface assembly of FIG. 1.

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the statement that two or more parts or components "engage" one another shall means that the parts exert a force against one another either directly or through one or more intermediate parts or components. As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such, the components of a "coupling assembly" may not be described at the same time in the following description.

As used herein, a "coupling" or "coupling component(s)" is one or more component(s) of a coupling assembly. That is, a coupling assembly includes at least two components that are structured to be coupled together. It is understood that the components of a coupling assembly are compatible with each other. For example, in a coupling assembly, if one coupling component is a snap socket, the other coupling component is a snap plug, or, if one coupling component is a bolt, then the other coupling component is a nut. As another example, the portions of two elements that are adhered to each other are a "coupling" or "coupling component(s)." Further, a "coupling" or "coupling component" may include an opening or passage through which another coupling passes.

As used herein, "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together. In that situation, the difference between the sizes of the components is even smaller whereby the amount of friction increases. If the element defining the opening and/or the component inserted into the opening are made from a deformable or compressible material, the opening may even be slightly smaller than the component being inserted into the opening. With regard to surfaces, shapes, and lines, two, or more, "corresponding" surfaces, shapes, or lines have generally the same size, shape, and contours.

As used herein, "a generally continuous seal" may have a gap or may gap when the user moves. As used herein, "a more complete seal" has a gap that is shorter in length than a gap of a generally continuous seal, or, is resistant to gapping when the user moves. As used herein, a "longitudinal axis" is not required to be a generally straight line. That is, a "longitudinal axis" as used herein is generally a centerline of a body which can include curves.

As used herein, the phrase "tension member" means a member capable of supporting a load while in tension, but which is generally flexible under a compressive force. As used herein, a "handle" is an element that is structured to be grasped by a human hand and/or finger(s). Thus, a "handle" is sized, shaped, and positioned, to be grasped by a human hand and/or finger(s). An element that is merely capable of being grasped by a human hand but which is not sized, shaped, and positioned, to be grasped by a human hand is not a "handle."

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 6:
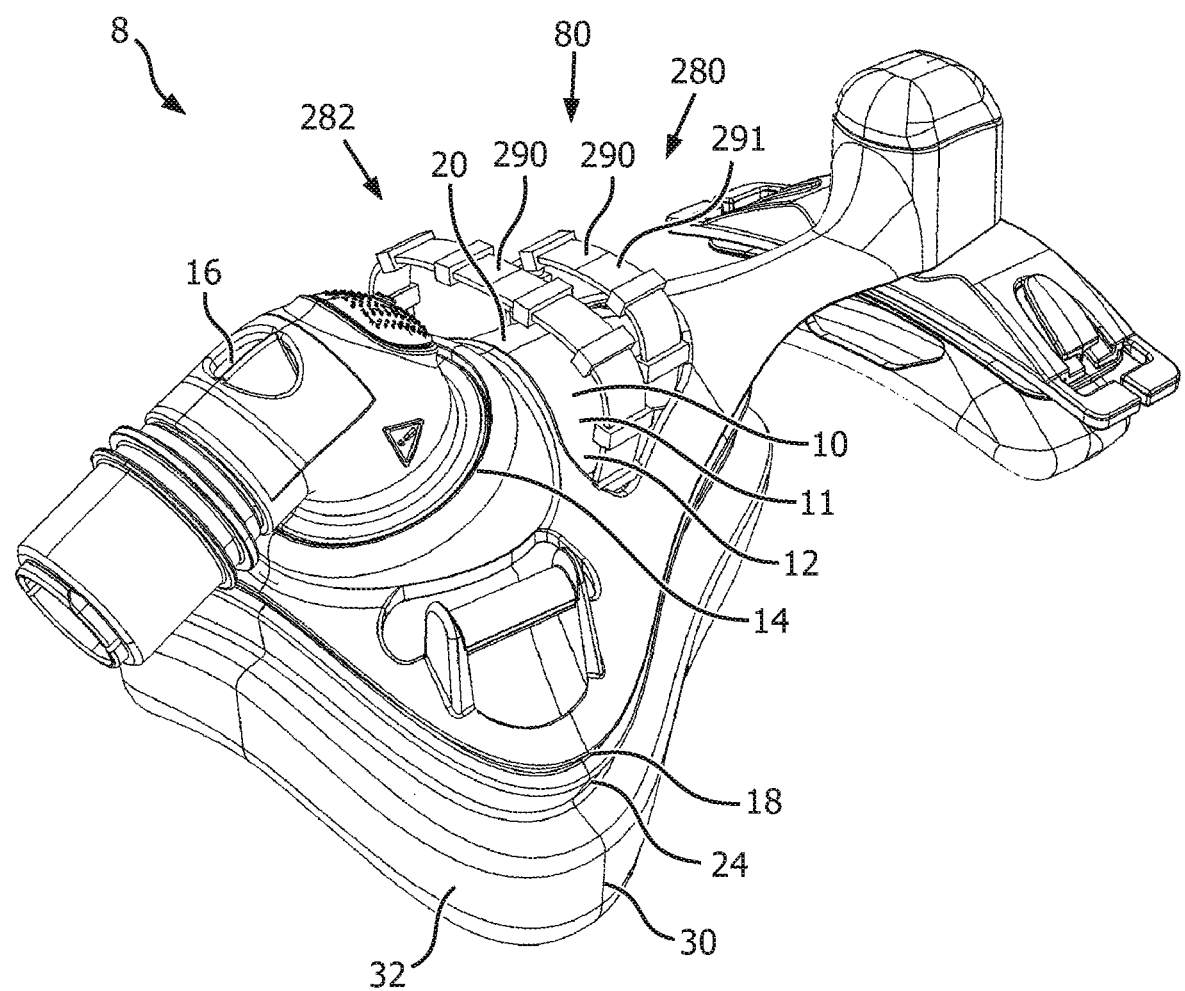
FIG. 6 is an isometric view of another embodiment of a respiratory interface assembly.
Figure 7:
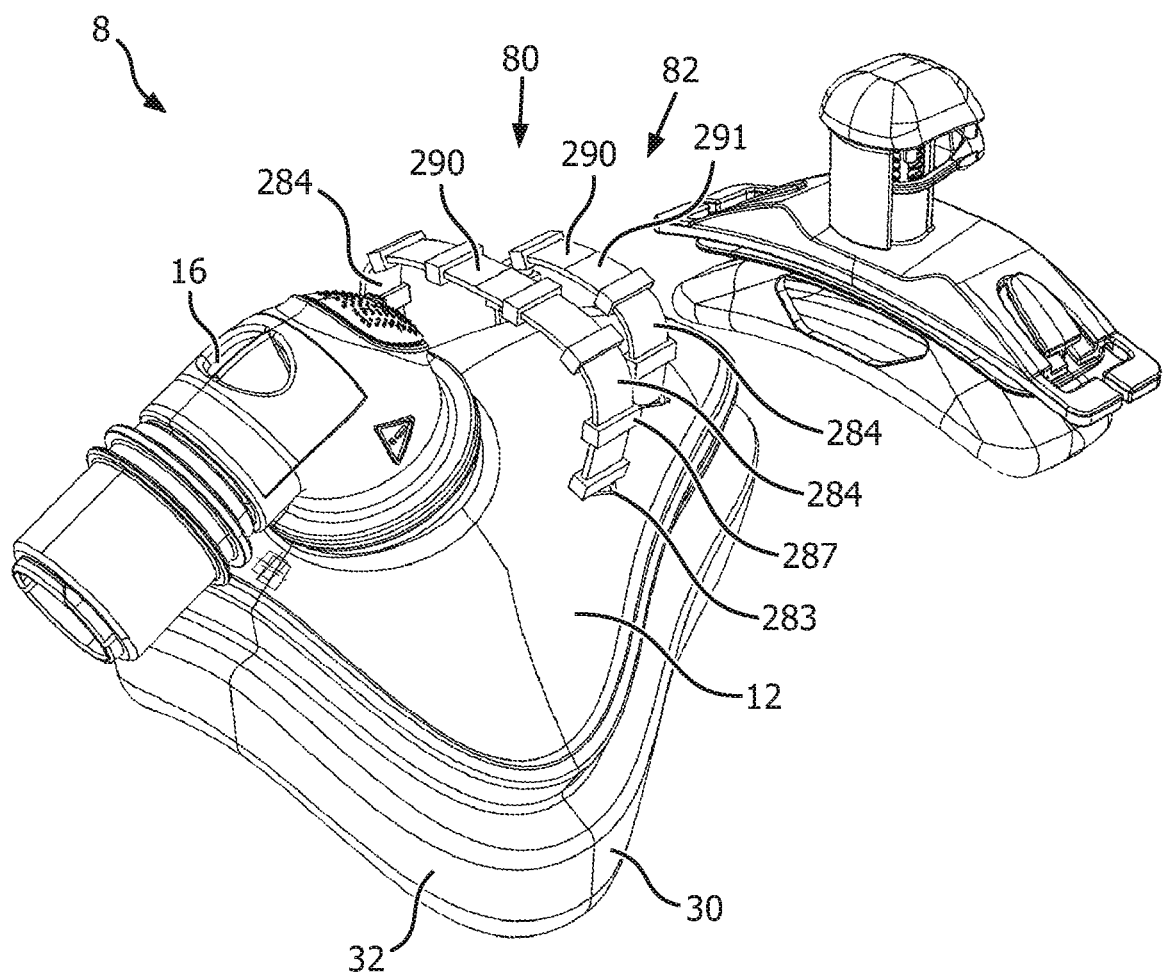
FIG. 7 is a partial isometric view of the respiratory interface assembly of FIG. 6.
Figure 8:
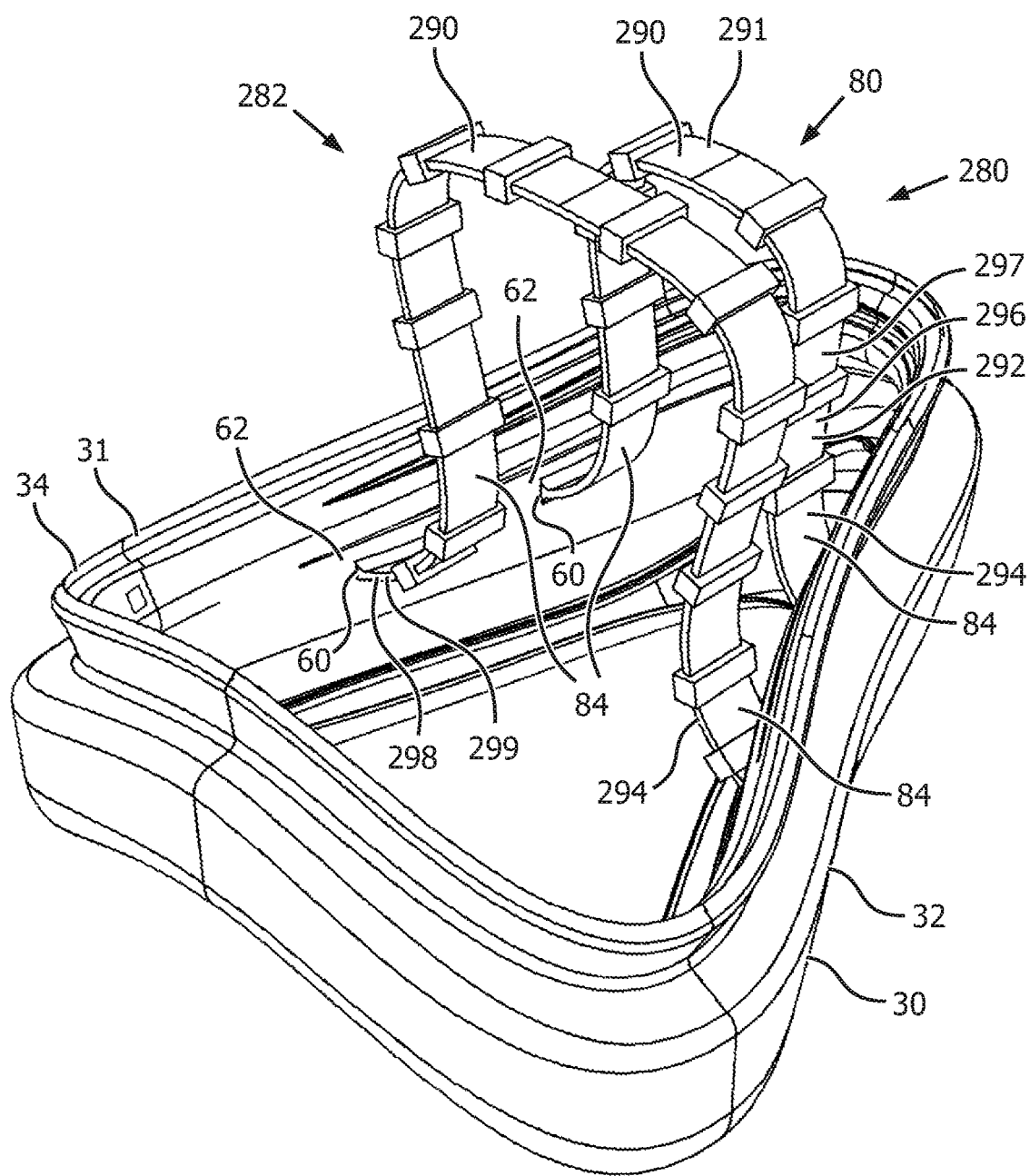
FIG. 8 is another partial isometric view of the respiratory interface assembly of FIG. 6.
Figure 9:
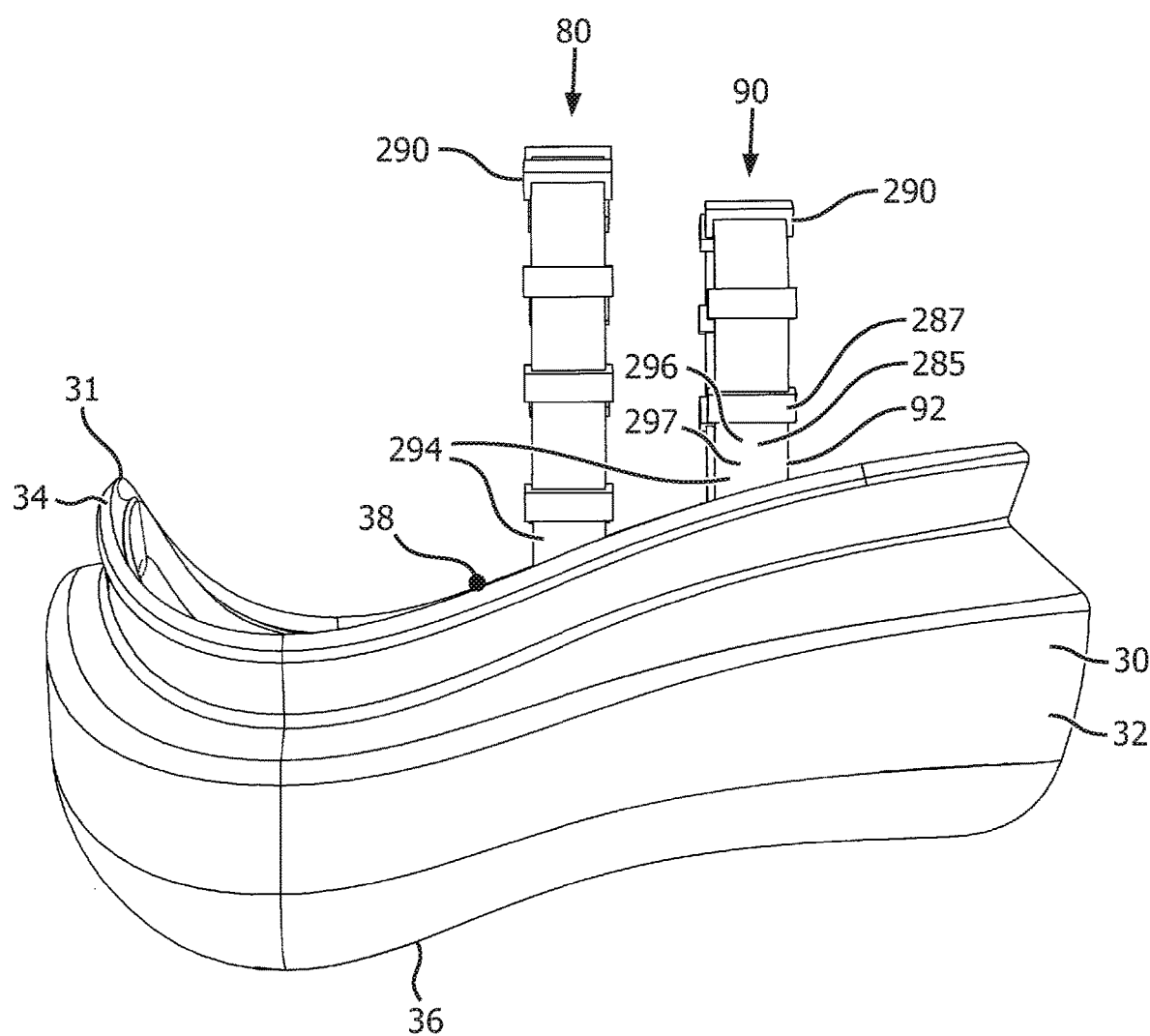
FIG. 9 is a partial side view of the respiratory interface assembly of FIG. 6.
Figure 10:
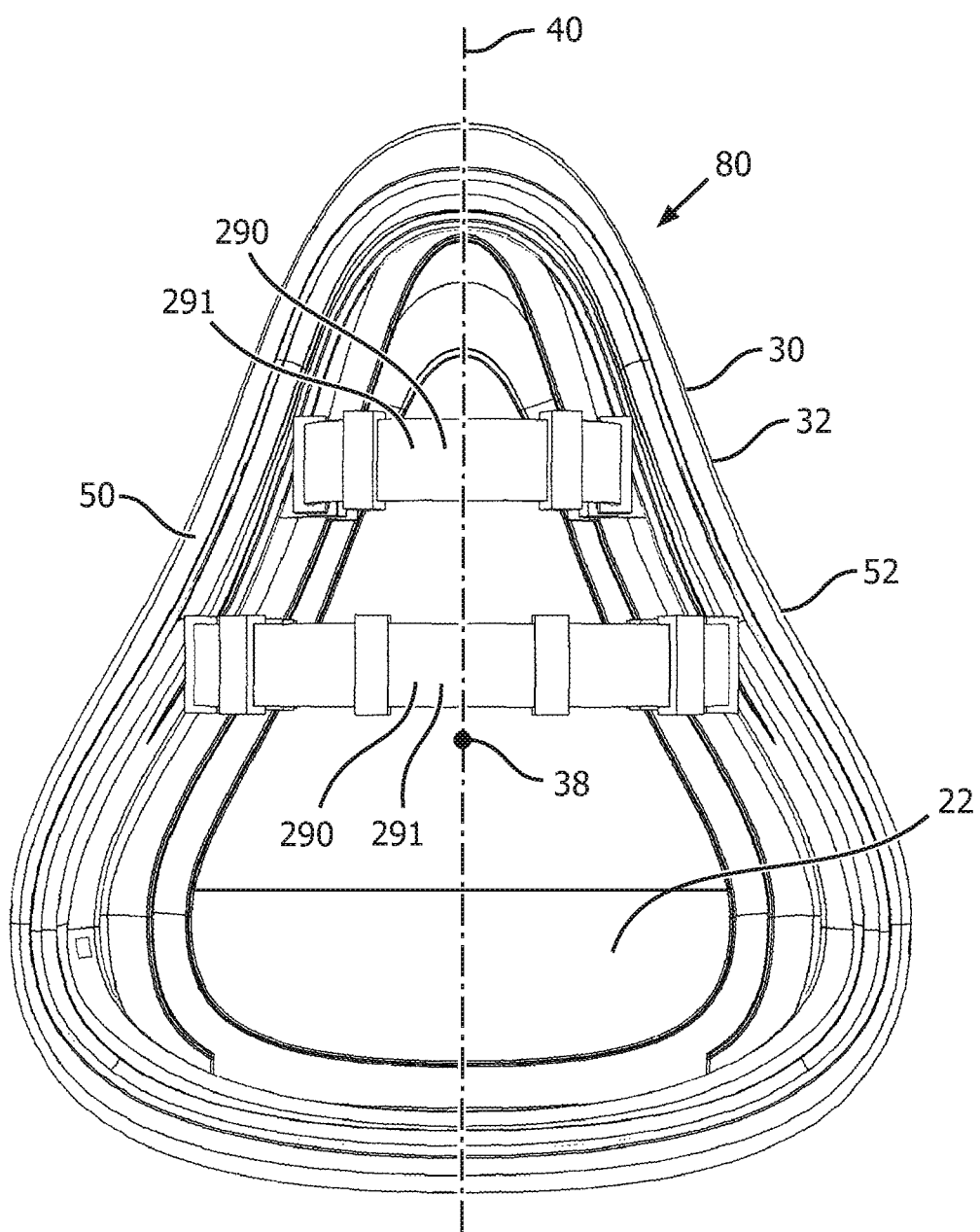
FIG. 10 is a partial front view of the respiratory interface assembly of FIG. 6.
Figure 11:
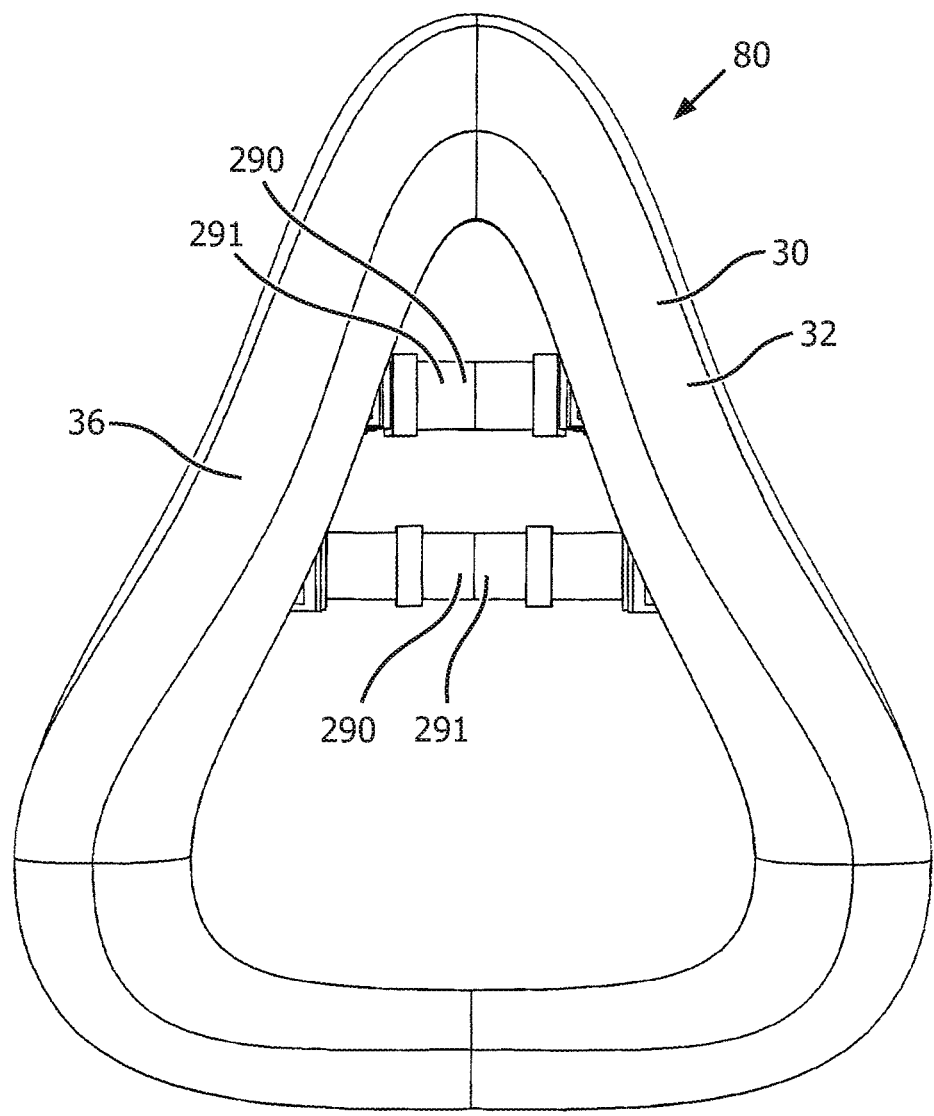
FIG. 11 is a partial back view of the respiratory interface assembly of FIG. 6.
Figure 12:
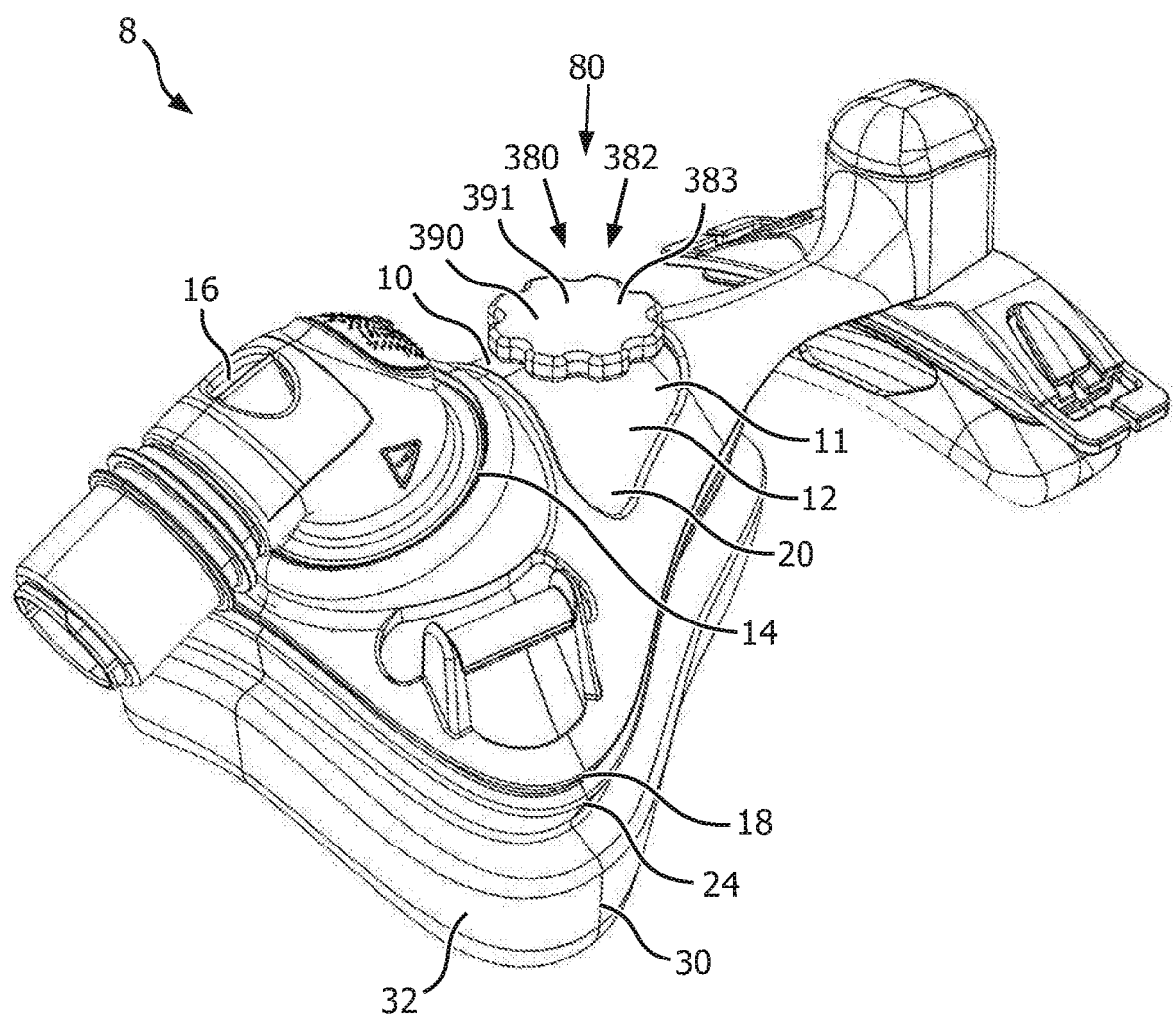
FIG. 12 is an isometric view of another embodiment of a respiratory interface assembly.
Figure 13:
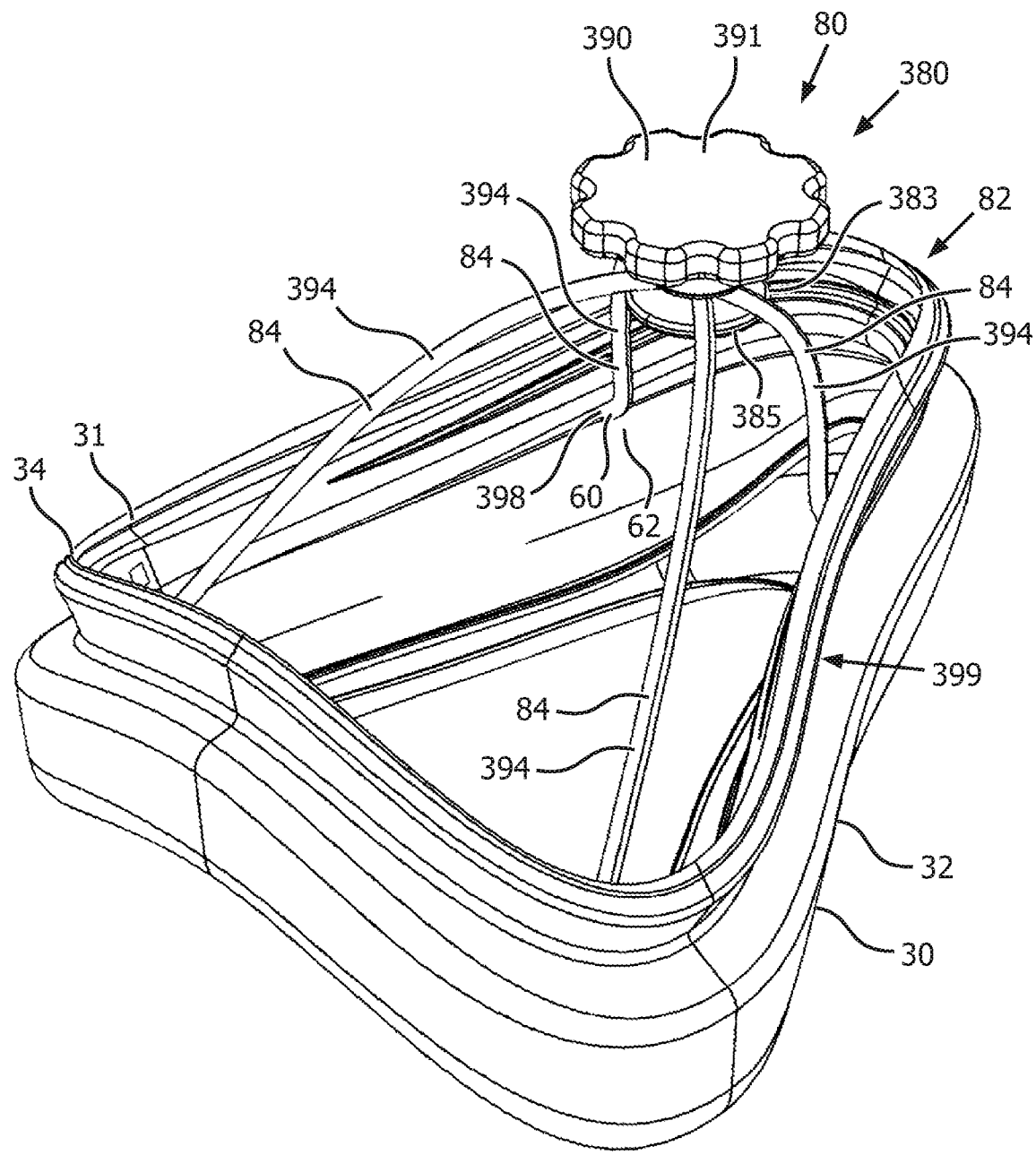
FIG. 13 is a partial isometric view of the respiratory interface assembly of FIG. 12.
Figure 14:
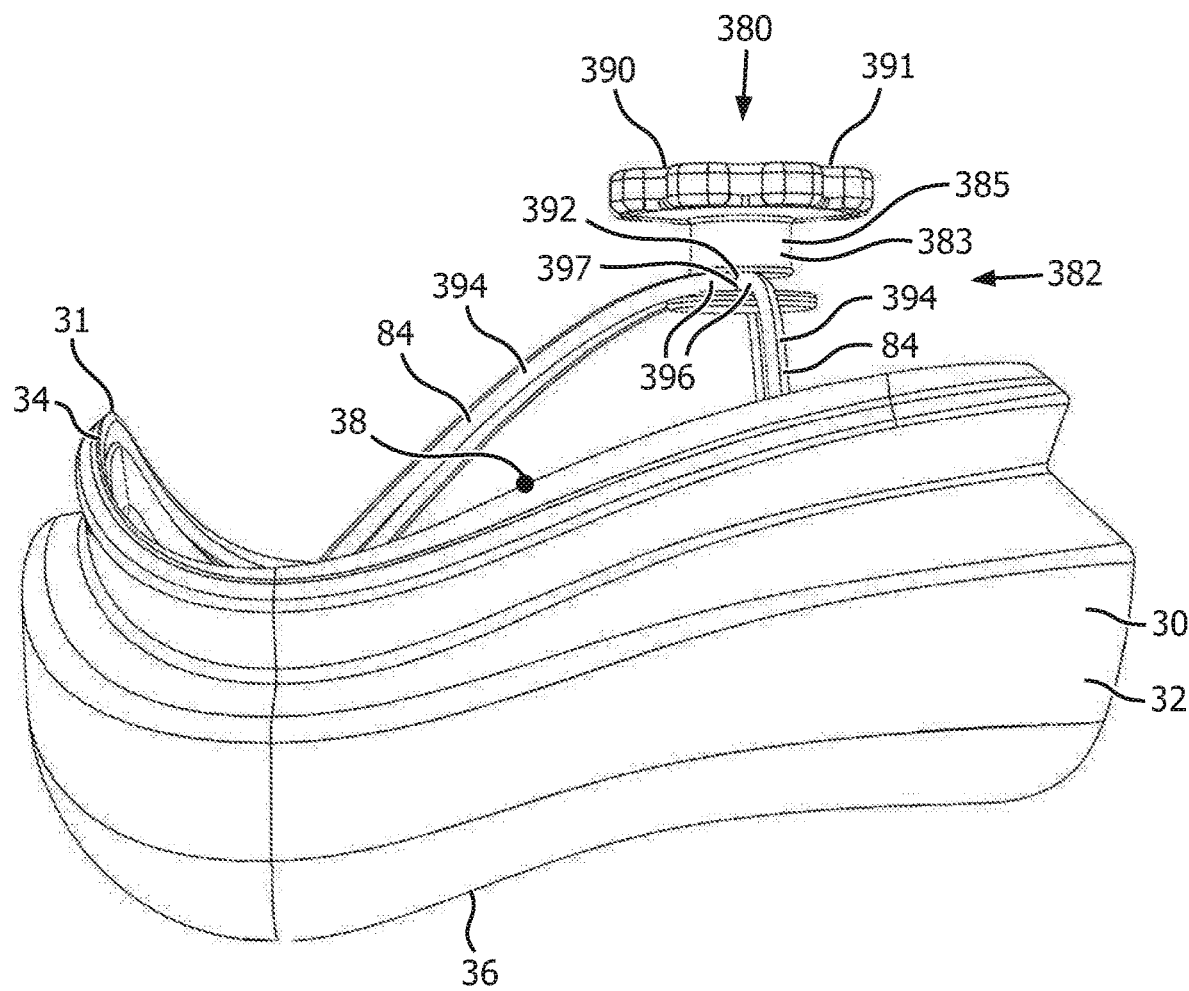
FIG. 14 is a partial side view of the respiratory interface assembly of FIG. 12.
Figure 15:
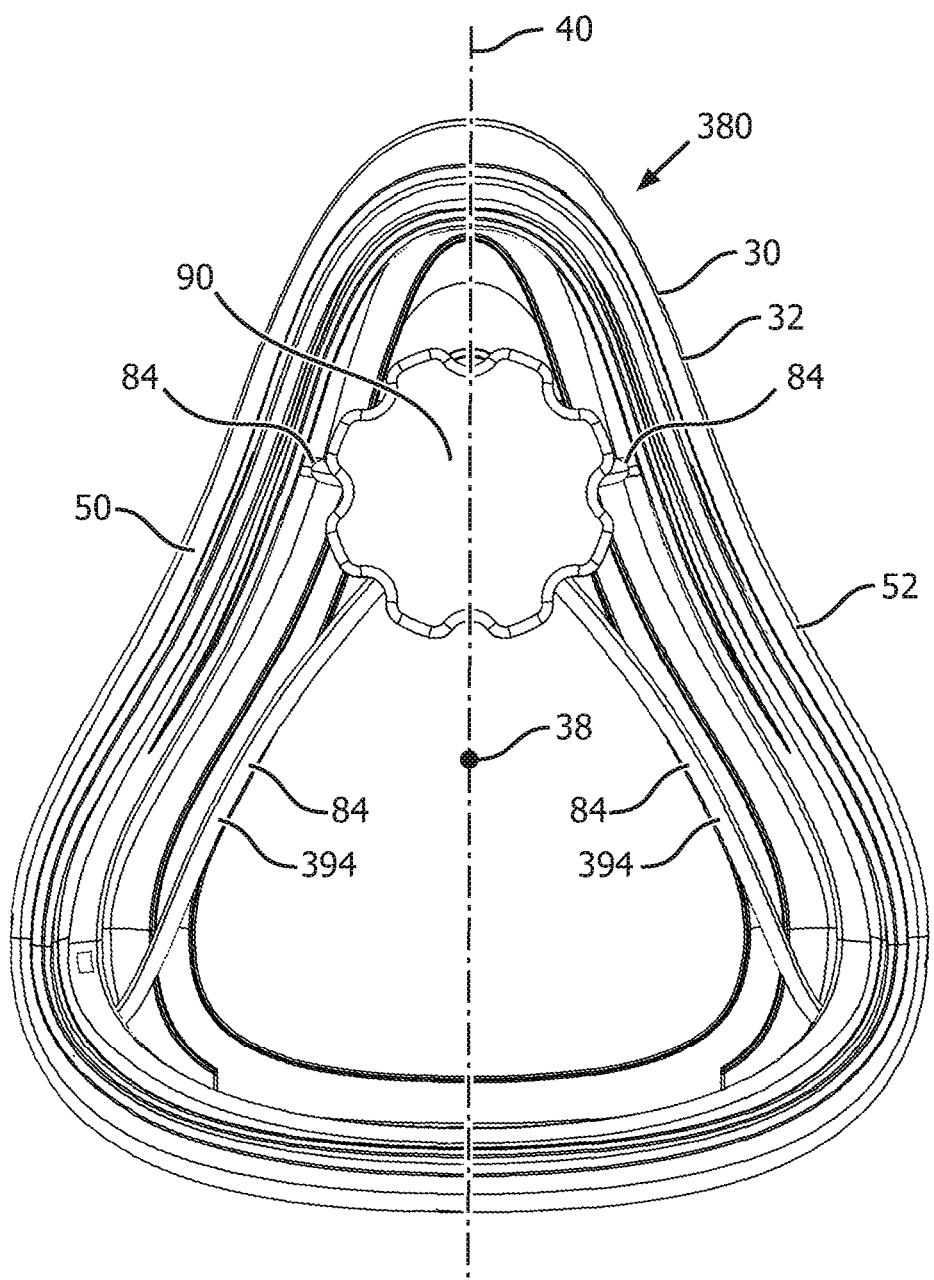
FIG. 15 is a partial front view of the respiratory interface assembly of FIG. 12.
Figure 16:
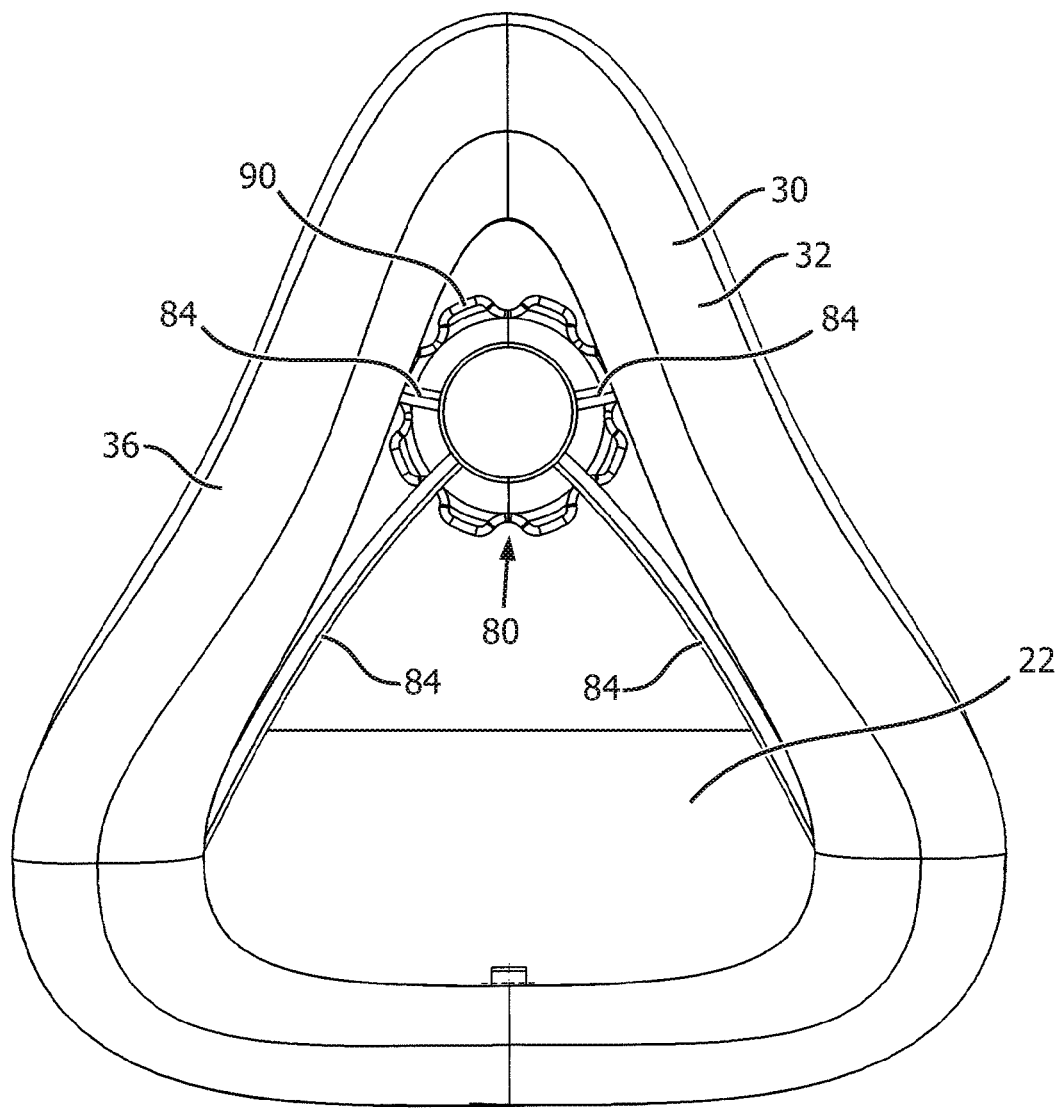
FIG. 16 is a partial back view of the respiratory interface assembly of FIG. 12.

FIGS. 1, 6, and 12 show a respiratory interface assembly 8 according to an embodiment of the invention. Respiratory interface assembly 8 includes a respiratory interface device 10 and a support assembly such as, but not limited to straps (not shown). Respiratory interface device 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™. device, Bi-Flex® device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

In an exemplary embodiment, the respiratory interface device 10 is a nasal and oral respiratory interface device 10 that is structured to be disposed over a user's nose and mouth. In another exemplary embodiment, not shown, respiratory interface device is a nasal respiratory interface device that is structured to be disposed over a user's nose. It is understood, however, that respiratory interface device 10 can include, without limitation, a nasal mask, nasal pillows, or any other device that provides a suitable gas flow communicating function. Thus, as used herein, the term "respiratory interface device" shall refer to any of such devices.

As shown in FIGS. 1-6, a nasal and oral respiratory interface device 10 includes a body 11 with a faceplate 12, a cushion 30, a cushion tension assembly 80. As is known, respiratory interface device 10 is structured to be coupled to a support assembly (not shown) such as, but not limited to a number of straps. Further, and as is known, respiratory interface device 10 is structured to be coupled to, and in fluid communication with, pressure generating system (not shown) via a patient circuit such as, but not limited to, a number of hoses. In an exemplary embodiment, respiratory interface device body faceplate 12 (hereinafter "faceplate" 12) is a substantially rigid body. In an exemplary embodiment, shown in FIG. 1, faceplate 12 is a single piece structured to cover the user's nose and mouth. That is, respiratory interface device 10 has a peripheral contour that is structured to extend over a user's nose and mouth. In this embodiment, respiratory interface device body 11 is coextensive with faceplate 12. Faceplate 12 defines lower opening 14.

Lower opening 14 can function as a gas inlet. Gas inlet (lower opening 14) can be coupled to a coupling device 16, such as a swivel conduit, for carrying gas such as air between respiratory interface device 10 and an external gas source (not shown), such as a blower, or any other suitable device. It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The coupling device may be any of a variety of different coupling devices that could be attached, either permanently or selectively, to lower opening 14 to carry gas to or from respiratory interface device 10. Thus, a variety of coupling devices (e.g., with or without swivels on one or both ends, and with or without an exhalation system formed integral to the device) may be used.

In an exemplary embodiment, faceplate 12 is generally convex or bowl-shaped. This shape defines an interior space that accommodates a user's nose and other features when respiratory interface device 10 is in use. Faceplate 12 includes a peripheral end 18 that extends about faceplate 12. In this exemplary embodiment, faceplate peripheral end 18 extends generally towards the user's face when respiratory interface device 10 is in use. Faceplate 12 includes an outer surface 20, an inner surface 22 (relative to the interior space). That is, as used herein and with reference to faceplate 12, "outer" or "outwardly" means away from the interior space defined by bowl-shaped faceplate 12, and, "inner" or "inwardly" means toward the interior space defined by bowl-shaped faceplate 12. As is known, faceplate 12 can be custom made to generally correspond to the user's facial contour. Faceplate 12, in an exemplary embodiment, includes a coupling component 24 such as, but not limited to a portion of faceplate 12 defining a groove (not shown) into which a tongue 31 on cushion body 32 may be inserted. Faceplate coupling component 24 is structured to couple cushion body 32, described below, to faceplate 12.

Respiratory interface device cushion 30 (hereinafter "cushion" 30) includes a body 32. Cushion body 32 can be constructed of a wide variety of resilient materials known in the art and can include, but is not limited to, a thermoplastic or thermoelastic material, including but not limited to an elastomer such as plastic, rubber, silicone, vinyl, foam, or any combination thereof. Cushion body 32 includes a coupling component 34, an engagement portion 36, a center 38, a centerline 40. The cushion body coupling component 34 is structured to couple the cushion body 32 to faceplate 12. As used herein, cushion body "centerline" 40 is a line extending generally vertically. That is, when respiratory interface device 10 is in use, cushion body centerline 40 generally corresponds to the centerline of the user's face; i.e. extending generally vertically over the user's nose. As used herein, cushion body "center" 38 is a point along the cushion body centerline 40 disposed about at the midpoint between the top of cushion body 32 and the bottom of cushion body 32. Further, cushion body "center" 38 is disposed along a line passing through cushion body coupling component 34. That is, when cushion body 32 is coupled to faceplate 12, cushion body "center" 38 is disposed along a generally horizontal line (as shown in FIGS. 3, 4, 9, 10, and 14, 15) that passes through the interface between faceplate coupling component 24 and cushion body coupling component 34.

Cushion body engagement portion 36 is structured to engage a user's face in a generally continuous seal. The resilient nature of cushion body 32 allows cushion body engagement portion 36 to be reconfigured so as to provide a more complete seal.

Cushion body 32 further includes a first nasal portion 50 and a second nasal portion 52. When respiratory interface device 10 is in use, cushion body first nasal portion 50 and cushion body second nasal portion 52 are disposed on either side of the user's nose. That is, cushion body first nasal portion 50 and cushion body second nasal portion 52 are offset to the right and to the left of cushion body centerline 40.

Cushion body 32 further includes a number of tension member coupling components 60. Each cushion body tension member coupling component 60 is structured to be coupled to a tension member cushion body coupling component 99, described below. Each cushion body tension member coupling component 60 has an associated selected portion 62 of cushion body 32, alternatively "cushion body selected portion 62." As used herein, a "selected portion 62 of cushion body 32" is that portion of cushion body 32 extending about, i.e. around, cushion body tension member coupling component 60.

Cushion tension assembly 80 is structured to alter the configuration of cushion body 32. As used herein, a "structured to alter the configuration of cushion body" means that an adjustment assembly 82, discussed below, is structured so that a mechanical action or motion must be deliberately actuated. That is, an assembly or device wherein movement of a cushion body 32, or a tension member 84 (discussed below) operatively coupled to a cushion body 32, is caused by the act of initializing utilization of respiratory interface device 10, i.e. placing a respiratory interface device 10 into an operating position over a user's face, is not an assembly or device and "structured to alter the configuration of cushion body," as used herein. In an exemplary embodiment, cushion tension assembly 80 is structured to alter the configuration of cushion body 32 from a first configuration, wherein cushion body 32 provides a generally continuous seal, and a second configuration wherein cushion body 32 provides a more complete seal.

In an exemplary embodiment, cushion tension assembly 80 includes an adjustment assembly 82 and a number of tension members 84. That is, in an exemplary embodiment, actuation of adjustment assembly 82 is structured to move cushion body 32 between a first configuration, wherein a selected portion 62 of cushion body 32 is a first distance from one of cushion body center 38 or cushion body centerline 40, and, a second configuration, wherein selected portion 62 of cushion body 32 is a second distance from one of cushion body center 38 or cushion body centerline 40. As used herein, an "actuation of [an] adjustment assembly structured to move cushion body" means that an adjustment assembly 82 is deliberately put into mechanical action or motion. That is, movement of a cushion body 32, or a tension member 84 operatively coupled to a cushion body 32, caused by the act of initializing utilization of respiratory interface device 10, i.e. placing a respiratory interface device 10 into an operating position over a user's face, is not an "actuation of [an] adjustment assembly structured to move cushion body," as used herein.

As set forth below, there are at least three embodiments of cushion tension assembly 80. Each embodiment shares a number of elements which are set forth below and wherein each embodiment is detailed further below. Adjustment assembly 82 is structured to change the effective length of at least one tension member 84. As used herein, the "effective length" is the length of a tension member 84 between tension member cushion body coupling component 99 and adjustment assembly 82. In each embodiment, adjustment assembly 82 includes a number of actuating devices 90 and number of tension member couplings 92. Each tension member coupling 92 is operatively coupled to at least one actuating device 90. Further, each actuating device 90 is disposed adjacent faceplate outer surface 20. As used herein, an element "disposed adjacent faceplate outer surface" means that faceplate 12 is not disposed between the element and the faceplate outer surface 20. That is, although an element located on the inner side of faceplate 12 may be near faceplate outer surface 20, such an element is not "disposed adjacent faceplate outer surface," as used herein. Similarly, each tension member coupling 92 is disposed adjacent the faceplate inner surface 22. As used herein, an element "disposed adjacent faceplate inner surface" means that faceplate 12 is not disposed between the element and the faceplate inner surface 22. That is, although an element located on the outer side of faceplate 12 may be near faceplate inner surface 22, such an element is not "disposed adjacent faceplate inner surface," as used herein.

Each tension member 84 includes an elongated body 94. Each tension member body 94 includes a first end 96 and a second end 98. Each tension member body first end 96 includes an adjustment assembly coupling component 97. Each tension member body adjustment assembly coupling component 97 is structured to be coupled, directly coupled, or operatively coupled, to adjustment assembly 82. Each tension member body second end 98 includes a tension member cushion body coupling component 99. Each tension member cushion body coupling component 99 is structured to be coupled, directly coupled, or operatively coupled, to cushion body 32.

As noted above, there are at least three embodiments of cushion tension assembly 80. Generally, the embodiments vary with the embodiment of adjustment assembly 82. In the exemplary embodiments, adjustment assembly 82 is selected from the group including, or limited to, a threaded rod adjustment assembly 182 (FIGS. 1-5), a notched strap adjustment assembly 282 (FIGS. 6-11), and a reel based closure adjustment assembly 382 (FIGS. 12-16). Hereinafter, elements associated with a threaded rod adjustment assembly 182 will have a reference number in the "100s," elements associated with a notched strap adjustment assembly 282 will have a reference number in the "200s," and, elements associated with a reel based closure adjustment assembly 382 will have a reference number in the "300s."

In a first exemplary embodiment, shown in Figures FIGS. 1-5, a cushion tension assembly 180 includes a threaded rod adjustment assembly 182 and a number of tension members 184 (two shown). In this embodiment, threaded rod adjustment assembly 182 includes a mounting member 185, a threaded rod 186, and an actuating device 190. Mounting member 185 includes a threaded passage 187 with threads corresponding to threaded rod 186. Threaded rod 186 includes a first end 181 and a second end 183. Actuating device 190, which in an exemplary embodiment is a knob 191, is coupled, directly coupled, or fixed to threaded rod first end 181. Threaded rod second end 183 includes a tension member coupling 192. In an exemplary embodiment, tension member coupling 192 is a flanged collar 193. As used herein, a "flanged collar" is a collar including a groove on an outer radial surface.

In this exemplary embodiment, tension members 184 includes two elongated, bodies 194 each with a first end 196 and a second end 198. In an exemplary embodiment, elongated bodies 194 are unitary; that is, elongated bodies 194 are joined at the respective first ends 196. Stated alternately, elongated bodies 194 share a first end 196. Further, in an exemplary embodiment, tension members 184 are also unitary with cushion body 32 It is noted that additional tension members 184 could be included. For example, four tension members (not shown) could be disposed in an X-shape.

A tension member adjustment assembly coupling component 197 is disposed at shared tension member body first end 196. In this exemplary embodiment, adjustment assembly coupling component 197 is a passage 197' sized to correspond to flanged collar 193. A tension member cushion body coupling component 199 is disposed at each tension member body second end 198. In an embodiment wherein tension members 184 are unitary with cushion body 32, cushion body tension member coupling component 60 and tension member cushion body coupling component 199 are the portions of cushion body 32 and tension members 184 at the interface between tension members 184 and cushion body 32. Alternatively, cushion body tension member coupling component 60 is a passage (not shown) through cushion body 32 and tension member cushion body coupling component 199 is a widened head (not shown) similar to the head of a nail. In this embodiment, tension member cushion body coupling component 199 is passed through cushion body tension member coupling component passage by stretching the cushion body 32 so as to allow the head to pass through cushion body tension member coupling component passage.

Mounting member 185 is coupled, directly coupled, or fixed to faceplate 12. Threaded rod 186 is operatively coupled to mounting member 185 by being disposed in threaded passage 187. Threaded rod first end 181 and knob 191 are disposed adjacent faceplate outer surface 20. Threaded rod second end 183 and tension member coupling 192 are disposed adjacent faceplate inner surface 22. Tension member adjustment assembly coupling component 197, i.e. passage 197', is coupled to flanged collar 193. Tension member cushion body coupling components 199 are coupled, directly coupled, or fixed, and are thereby operatively coupled, to cushion body 32 at cushion body tension member coupling component 60. In an exemplary embodiment, tension member cushion body coupling components 199 and cushion body tension member coupling component 60 are disposed at cushion body first nasal portion 50 and cushion body second nasal portion 52.

In this configuration, actuation of adjustment assembly 182, i.e. turning knob 191, causes threaded rod 186 to move in/out of the cushion body 32 interior space. Further, as threaded rod 186 moves in/out of the cushion body 32 interior space, threaded rod second end 183 moves away from or toward, respectively, faceplate 12. As threaded rod second end 183 moves, tension members 184 are also moved away from or toward, respectively, faceplate 12. Because tension member cushion body coupling components 199 are coupled to (or directly coupled to, fixed to, or unitary with) cushion body 32, cushion body 32 also moves between a first configuration, wherein cushion body 32 provides a generally continuous seal, and a second configuration wherein cushion body 32 provides a more complete seal.

Stated alternately, actuation of adjustment assembly 82, i.e. turning knob 191, moves cushion body 32 between a first configuration, wherein a selected portion 62 of cushion body 32 is a first distance from one of the cushion body center 38 or cushion body centerline 40, and, a second configuration, wherein the selected portion 62 of cushion body 32 is a second distance from one of the cushion body center 38 or cushion body centerline 40. Stated alternately, actuation of adjustment assembly 182, i.e. turning knob 191, moves cushion body 32 between a first configuration, wherein first nasal portion 50 and second nasal portion 52 are a first distance from one of cushion body center 38 or cushion body centerline 40, and, the second configuration, wherein first nasal portion 50 and second nasal portion 52 are a second distance from one of cushion body center 38 or cushion body centerline 40. In this embodiment, adjustment assembly 182 is not unitary with any tension member 184.

In a second embodiment, shown in Figures FIGS. 6-11, cushion tension assembly 280 includes a notched strap adjustment assembly 282. In this embodiment, adjustment assembly 282 is partially unitary with tension member(s) 284 (four shown). That is, in this embodiment, adjustment assembly actuating device 290 is a number of handles 291 (two shown) that is unitary with tension members 284 (i.e. one handle 291 is unitary with two tension members 284). That is, a handle tension member coupling 292 is an interface between handle 291 and tension members 284. Adjustment assembly 282 further includes a number of latching passages 283 in the faceplate 12. As used herein, "latching passage" is a passage having a smaller cross-sectional area that a portion of a tension member passes therethrough. Further, a "latching passage" is made from, or is associated with a tension member made from, a resilient material.

In this embodiment, there are two tension members 284 including resilient bodies 294 each with a first end 296 and a second end 298. Further, a medial portion 285 of each tension member body 294 includes a number of protuberances 287. As used herein, a "protuberance" is a portion of an elongated tension member having a greater cross-sectional area than other portions of the tension member. A tension member adjustment assembly coupling component 297 is disposed at each tension member body first end 296. A tension member cushion body coupling component 299 is disposed at each tension member body second end 298. In this embodiment, each tension member body 294 is unitary with adjustment assembly actuating device 290, i.e. handle 291. That is, in an exemplary embodiment, each tension member adjustment assembly coupling component 297 is an interface 297' between handle tension member coupling 292 and tension member body first end 296. Further, in an exemplary embodiment, tension member body 294 is unitary with cushion body 32. Thus, in this embodiment wherein tension members 284 are unitary with cushion body 32, cushion body tension member coupling component 60 and tension member cushion body coupling component 299 are the portions of cushion body 32 and tension members 284 at the interface between tension members 284 and cushion body 32.

Alternatively, cushion body tension member coupling component 60 is a passage (not shown) through cushion body 32 and tension member cushion body coupling component 299 is a widened head (not shown) similar to the head of a nail. In this embodiment, tension member cushion body coupling component 299 is passed through cushion body tension member coupling component passage by stretching the cushion body 32 so as to allow the head to pass through cushion body tension member coupling component passage. In an exemplary embodiment, tension member cushion body coupling components 299 and cushion body tension member coupling component 60 are disposed at cushion body first nasal portion 50 and cushion body second nasal portion 52.

In this embodiment, each tension member body medial portion 285 is passed through latching passages 283. In an exemplary embodiment, there are two latching passages 283 for each tension member. 284. Each latching passage 283 is offset, i.e. spaced, from cushion body centerline 40. Further, each tension member cushion body coupling component 299 is coupled to cushion body 32 as described above. Further, each tension member adjustment assembly coupling component 297 is unitary with adjustment assembly actuating device 290, i.e. handle 291.

Accordingly, adjustment assembly actuating device 290, i.e. handle(s) 291, are disposed adjacent faceplate outer surface 20. Each handle tension member coupling 292 is disposed adjacent faceplate inner surface 22. Tension member cushion body coupling components 299 are coupled, directly coupled, or fixed, and are thereby operatively coupled, to cushion body 32 at cushion body tension member coupling component 60.

In this configuration, a user actuates adjustment assembly 282 by pulling or pushing on adjustment assembly actuating device 290, i.e. handle 291. Actuating adjustment assembly 282 causes tension members 284 to move through latching passages 283. That is, resilient protuberances 287 deform and pass through latching passages 283. When adjustment assembly 282 is not actuated, there is insufficient bias to deform resilient protuberances 287. Thus, when adjustment assembly 282 is not actuated resilient protuberances 287 engage the faceplate 12 at latching passages 283 and resist movement of tension members 284. It is further noted that, and as used herein, the portion of the unitary handle 291 and tension members 284 identifiable as handle 291 changes as the user actuates adjustment assembly 282. That is, as used herein, the "handle" 291 is the portion of unitary handle 291 and tension members 284 that the user may grasp, i.e. the portion of unitary handle 291 and tension members 284 that is adjacent faceplate outer surface 20. Thus, for example, as the user pulls on handle 291, the portion of unitary handle 291 and tension members 284 disposed adjacent faceplate outer surface 20 becomes longer; thus, handle 291 becomes longer and each tension member 284 becomes shorter. Thus, it is understood, and as used herein, that the location of each tension member adjustment assembly coupling component 197 and handle tension member coupling 292 changes based upon the configuration of the unitary handle 291 and tension members 284 relative to faceplate 12. That is, as used herein, interface 197" between handle tension member coupling 292 and tension member body first end 296, as well as tension member adjustment assembly coupling component 197, is always located at faceplate 12.

Accordingly, because tension member cushion body coupling components 299 are coupled to (or directly coupled to, fixed to, or unitary with) cushion body 32, cushion body 32 also moves between a first configuration, wherein cushion body 32 provides a generally continuous seal, and a second configuration wherein cushion body 32 provides a more complete seal. Stated alternately, actuation of adjustment assembly 282, i.e. pulling/pushing handle 291, moves cushion body 32 between a first configuration, wherein a selected portion 62 of cushion body 32 is a first distance from one of the cushion body center 38 or cushion body centerline 40, and, a second configuration, wherein the selected portion 62 of cushion body 32 is a second distance from one of the cushion body center 38 or cushion body centerline 40. Stated alternately, actuation of adjustment assembly 282, i.e. pulling/pushing handle 291, moves cushion body 32 between a first configuration, wherein first nasal portion 50 and second nasal portion 52 are a first distance from one of cushion body center 38 or cushion body centerline 40, and, the second configuration, wherein first nasal portion 50 and second nasal portion 52 are a second distance from one of cushion body center 38 or cushion body centerline 40.

In a third exemplary embodiment, shown in FIGS. 12-16, a reel based closure adjustment assembly 382 includes a reel based closure device 383. A reel based closure device 383 is a device such as those disclosed in U.S. Pat. Nos. 8,516,662; 8,424,168; 8,091,182; and 7,954,204. The details of such devices, and their operation, are not relevant to the present disclosure. It is noted that a reel based closure device 383 includes an actuating device 390, which in an exemplary embodiment is a knob 391. Further, a reel based closure device 383 includes a reel (not shown) about which a number of tension members 384 are wrapped. For this disclosure, it is noted that a cushion tension assembly 380 includes reel based closure adjustment assembly 382 and a number of tension members 384 (four shown). In this embodiment, reel based closure adjustment assembly 382 includes a housing assembly 385, a reel (not shown), and an actuating device 390. Actuating device 390, which in an exemplary embodiment is a knob 391, is rotatably coupled, directly coupled, or fixed to housing assembly 385. Actuating device 390, i.e. knob 391, is fixed to the reel. Thus, rotation of the actuating device 390, i.e. knob 391, causes reel to rotate within housing assembly 385. Reel includes a tension member coupling 392, shown schematically.

In this exemplary embodiment, tension members 384 includes four elongated, bodies 394 each with a first end 396 and a second end 398. A tension member adjustment assembly coupling component 397 is disposed at each tension member body first end 396. A tension member cushion body coupling component 399 is disposed at each tension member body second end 398. In an exemplary embodiment, tension members 384 are adhered to cushion body 32. In an embodiment wherein tension members 384 are adhered to cushion body 32, cushion body tension member coupling component 60 and tension member cushion body coupling component 399 are the portions of cushion body 32 and tension members 384 at the interface between tension members 384 and cushion body 32. Alternatively, cushion body tension member coupling component 60 is a passage (not shown) through cushion body 32 and tension member cushion body coupling component 399 is a widened head (not shown) similar to the head of a nail. In this embodiment, tension member cushion body coupling component 399 is passed through cushion body tension member coupling component passage by stretching the cushion body 32 so as to allow the head to pass through cushion body tension member coupling component passage.

Housing assembly 385 is coupled, directly coupled, or fixed to faceplate 12. Knob 391 is disposed adjacent faceplate outer surface 20. Reel tension member coupling 392 is disposed adjacent faceplate inner surface 22. Tension member cushion body coupling components 399 are coupled, directly coupled, or fixed, and are thereby operatively coupled, to cushion body 32 at cushion body tension member coupling component 60. In an exemplary embodiment, tension member cushion body coupling components 399 and cushion body tension member coupling component 60 are disposed at cushion body first nasal portion 50 and cushion body second nasal portion 52.

In this configuration, actuation of adjustment assembly 382, i.e. turning knob 391, causes reel to rotate in housing assembly 385. This action winds, or unwinds, tension members 384 about reel. Because tension member cushion body coupling components 399 are coupled to (or directly coupled to, fixed to, or unitary with) cushion body 32, cushion body 32 also moves between a first configuration, wherein cushion body 32 provides a generally continuous seal, and a second configuration wherein cushion body 32 provides a more complete seal. Stated alternately, actuation of adjustment assembly 82, i.e. turning knob 391, moves cushion body 32 between a first configuration, wherein a selected portion 62 of cushion body 32 is a first distance from one of the cushion body center 38 or cushion body centerline 40, and, a second configuration, wherein the selected portion 62 of cushion body 32 is a second distance from one of the cushion body center 38 or cushion body centerline 40. Stated alternately, actuation of adjustment assembly 382, i.e. turning knob 391, moves cushion body 32 between a first configuration, wherein first nasal portion 50 and second nasal portion 52 are a first distance from one of cushion body center 38 or cushion body centerline 40, and, the second configuration, wherein first nasal portion 50 and second nasal portion 52 are a second distance from one of cushion body center 38 or cushion body centerline 40. In this embodiment, adjustment assembly 382 is not unitary with any tension member 384.

Figure 17:
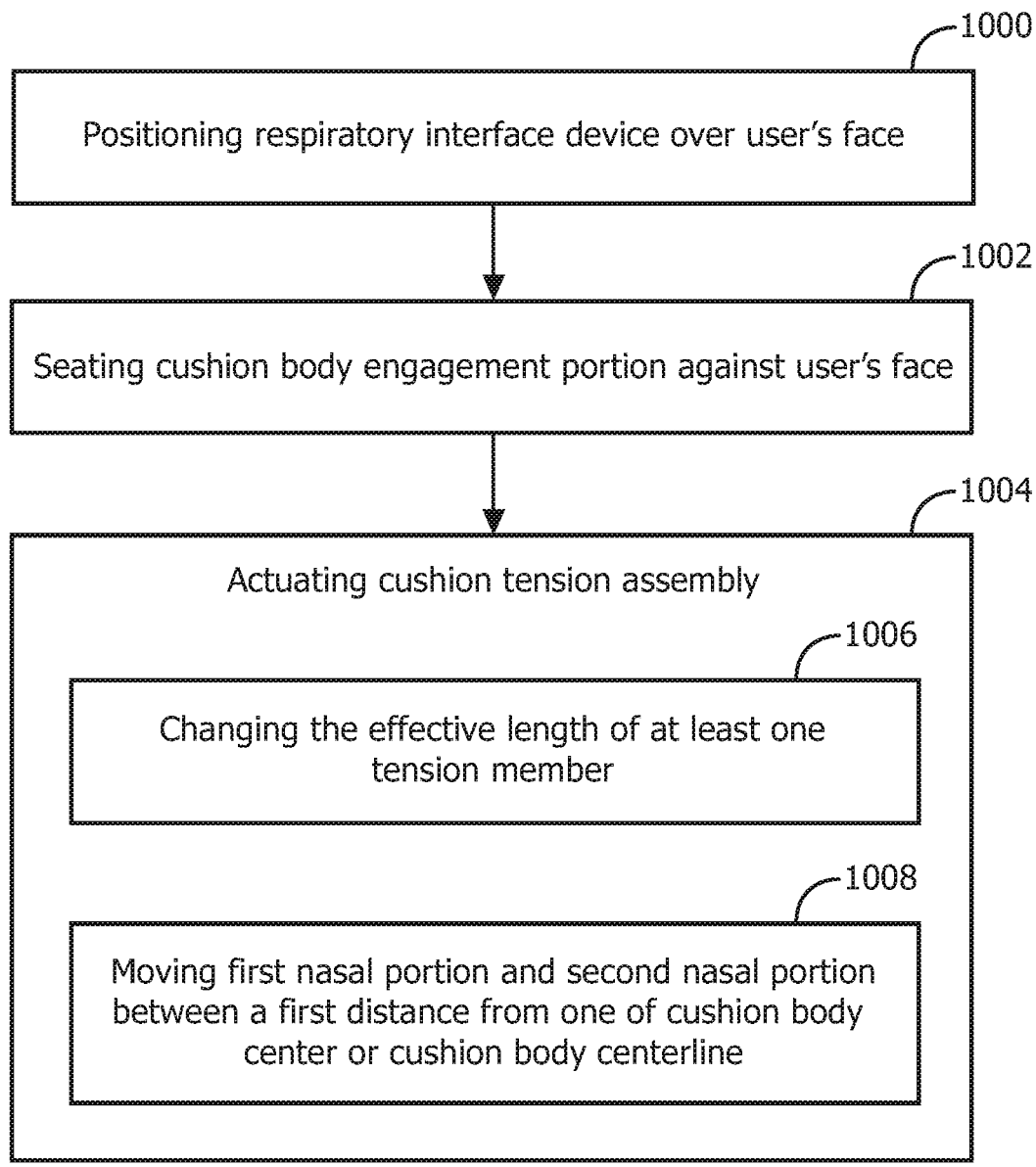
FIG. 17 is a flowchart of the disclosed method.

As shown in FIG. 17, a method of using a respiratory interface device 10 including a cushion tension assembly 80, or any of the identified embodiments of cushion tension assembly 180, 280, 380, as described above, includes the following. Positioning 1000 respiratory interface device 10 over user's face, seating 1002 cushion body engagement portion 36 against user's face so that cushion body engagement portion 36 provides a generally continuous seal, and, actuating 1004 cushion tension assembly 80, 180, 280, 380 so that cushion body 32 moves between a first configuration and a second configuration. Further, actuating 1004 cushion tension assembly 80, 180, 280, 380 so that cushion body 32 moves between a first configuration and a second configuration includes changing 1006 the effective length of at least one tension member 84, 184, 284, 384. Further, actuating 1004 cushion tension assembly 80, 180, 280, 380 so that cushion body 32 moves between a first configuration and a second configuration includes moving 1008 first nasal portion 50 and second nasal portion 52 between a first distance from one of cushion body center 38 or cushion body centerline 40, and, a second distance from one of cushion body center 38 or cushion body centerline 40.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by on and the same item of hardware. The word "a" or "an" preceding an element does not exclude the presence of a plurality of such elements. In any device claim enumerating several means, several of these means may be embodied by one and the same item of hardware The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device comprising:
a faceplate including an inner surface and an outer surface;
a cushion including a resilient body, the body including a center, a centerline, and an engagement portion structured to engage a user's face, wherein the cushion body is coupled to the faceplate;
a cushion tension assembly including an adjustment assembly and a number of tension members,
wherein each tension member is operatively coupled to the adjustment assembly,
wherein each tension member is operatively coupled to the cushion body, and
wherein the adjustment assembly is structured to move the cushion body between a first configuration in which the cushion body provides a generally continuous seal, and a second configuration in which the cushion body provides a more complete seal;
wherein the adjustment assembly is coupled to the faceplate,
wherein the adjustment assembly includes a number of actuating devices and number of tension member couplings, and
wherein each tension member coupling is coupled to a tension member,
wherein each tension member coupling is operatively coupled to at least one actuating device,
wherein each actuating device is disposed adjacent the faceplate outer surface, and wherein each tension member coupling is disposed adjacent the faceplate inner surface,
wherein the cushion body includes a number of tension member couplings,
wherein each cushion body tension member coupling includes an associated selected portion of the cushion body,
wherein the adjustment assembly is structured to move the cushion body between the first configuration in which the cushion body tension member coupling selected portion of the cushion body is a first distance from one of the cushion body center or cushion body center line, and the second configuration in which the cushion body tension member coupling selected portion of the cushion body is a second distance from one of the cushion body center or cushion body centerline.

2. The respiratory interface device of claim 1, wherein the adjustment assembly is selected from the group including a threaded rod adjustment assembly, a notched strap adjustment assembly, and a reel based closure adjustment assembly.

3. The respiratory interface device of claim 1, wherein the adjustment assembly is structured to change the effective length of at least one tension member.

4. The respiratory interface device of claim 1, wherein each tension member includes an elongated body, wherein each tension member body includes a first end and a second end, wherein each tension member body first end is operatively coupled to the adjustment assembly, and wherein each tension member body second end is operatively coupled to the cushion body.

5. The respiratory interface device of claim 1, wherein the adjustment assembly is not unitary with any tension member.

6. The respiratory interface device of claim 1, wherein the cushion body includes a first nasal portion and a second nasal portion, and wherein the adjustment assembly is structured to move the cushion body between the first configuration in which the first nasal portion and the second nasal portion are a first distance from one of the cushion body center or cushion body centerline, and the second configuration in which the first nasal portion and the second nasal portion are a second distance from one of the cushion body center or cushion body centerline.

* * * * *